United States Patent [19]

Hubbard, Jr.

[11] Patent Number: 6,009,875

[45] Date of Patent: *Jan. 4, 2000

[54] USE OF SYMPATHETIC ANTAGONISTS FOR TREATMENT OF CHRONIC MUSCLE PAIN

[75] Inventor: David R. Hubbard, Jr., San Diego, Calif.

[73] Assignee: Berlex Laboratories, Inc., Wayne, N.J.

[*] Notice: This patent is subject to a terminal disclaimer.

[21] Appl. No.: 08/325,987

[22] Filed: Oct. 19, 1994

Related U.S. Application Data

[63] Continuation-in-part of application No. 08/138,453, Oct. 14, 1993, Pat. No. 5,513,661.

[30] Foreign Application Priority Data

Oct. 14, 1994 [WO] WIPO ............... PCT/US94/11615

[51] Int. Cl.[7] .................................................. A61B 19/00
[52] U.S. Cl. ............................................................ 128/898
[58] Field of Search ........................................ 128/597–9

[56] References Cited

U.S. PATENT DOCUMENTS

| | | | |
|---|---|---|---|
| 2,599,000 | 6/1952 | Kerwin et al. | 260/570.7 |
| 5,447,947 | 9/1995 | Campbell | 514/392 |
| 5,513,661 | 5/1996 | Hubbard | 128/898 |

FOREIGN PATENT DOCUMENTS 0 120 165   10/1984   European Pat. Off. .

OTHER PUBLICATIONS

Ashburn & Fine, *Comprehensive Therapy* (1990) 16:37–42.

Stav et al., *Am. J. Acupuncture* (1991) 19:29–31.

*Primary Examiner*—John P. Lacyk
*Attorney, Agent, or Firm*—Millen, White, Zelane, & Branigan, P.C.

[57] ABSTRACT

Methods are provided for intramuscular needle diagnosis and treatment of muscle pain that is the result of sympathetically mediated spindle spasm. Two simultaneous needle EMG needle recordings are used to establish the presence of and magnitude of the "trigger points" in painful muscle. The abnormal muscle activity so identified is then treated by blocking the sympathetic activation of the muscle with an agent that inhibits sympathetic transmission.

61 Claims, 9 Drawing Sheets

USE OF SYMPATHETIC ANTAGONISTS FOR TREATMENT OF CHRONIC MUSCLE PAIN

CROSS-REFERENCE TO RELATED APPLICATIONS

This application is a continuation-in-part of U.S. application Ser. No. 08/138,453, filed Oct. 14, 1993, now U.S. Pat. No. 5,513,661 which disclosure is incorporated herein by reference.

INTRODUCTION

1. Technical Field

This invention relates generally to treatment of chronic muscle pain using adrenergic antagonists. The method is exemplified by injection of phenoxybenzamine directly into neuromuscular abnormalities such as myofascial trigger points.

2. Background of the Invention

Chronic muscle pain, which may comprise pain associated with headaches, neck and lower back problems, fibromyalgia, temporomandibular disorders and myofascial pain syndromes, has been described as epidemic (Sola, A. and Bonica, J. (1990) *Management of Pain*, Philadelphia, Lea & Febiger). One common type of chronic muscle pain, myofascial pain syndrome, is a neuromuscular dysfunction of skeletal muscle fibers manifested by neuromuscular abnormalities. Examples of such neuromuscular abnormalities include trigger point (TrP) and tender point (TeP) phenomena of various origins. Myofascial pain syndrome is a neuromuscular dysfunction of skeletal muscle fibers manifested by trigger point (TrP) phenomena of various origins and referred phenomena.

The underlying pathophysiology of TrPs has not been conclusively established. However, specific criteria have been defined for identifying TrPs (Simons, D., (1990) *Adv. Pain Res. Ther.* 17:1:41; Travell et al. *Myofascial Pain and Dysfunction, the Trigger Point Manual*, New York; Williams & Wilkins (1983); 5–44. These criteria include a palpable firm area of muscle, referred to as the taut band; within the taut band, a localized spot of exquisite tenderness to manual pressure, the TrP; a characteristic pattern of pain, tingling, or numbness in response to sustained pressure on the TrP within the taut band; and a local twitch of the taut band when the TrP is distorted transversely. Although the taut band may be several centimeters long, the TrP itself is reported to be only a few millimeters in diameter. The referral phenomena include referred pain, referred tenderness, or referred autonomic phenomena, such as vasoconstriction, coldness, sweating, pilomotor response, ptosis and hypersecretion.

There are both active TrPs that cause clinical pain syndromes, and latent TrPs, which are painless, and not associated with clinical pain syndromes. Latent TrPs are, like active ones, identified by manual palpation of taut bands, tenderness, and characteristic referral pattern of pain in response to sustained manual pressure. Fifty percent of asymptomatic persons have latent TrPs on examination of the shoulder-girdle musculature. Sola et al. (1955) *Am. J. Phys. Med.* 34:585–90. TrPs can also be distinguished from Tender points (TePs). Tender points are areas of tenderness that may or may not be in muscle tissue, do not have palpable taut bands, and do not refer pain to adjacent areas. Travell et al., *Myofascial Pain and Dysfunction, The Trigger Point Manual*, New York; Williams & Wilkins (1983), 5–44.

Patients with a variety of chronic muscle pain syndromes, including tension headaches, neck and lower back problems, fibromyalgia and myofascial pain syndromes present with TrPs in their muscles. An efficacious method of identification and treatment of chronic muscle pain is needed, particularly a treatment which provides long-lasting and/or permanent pharmacologic blockade of trigger point pain and related symptoms. It therefore also is of interest to determine whether there is spontaneous electromyography (EMG) activity in TrPs, and to monitor and eliminate the cause of this EMG activity as a means for devising treatment regimens for chronic muscle pain.

Relevant Literature

Muscle biopsy studies of TrPs have searched for areas of tissue damage (Yunus, et al. (1981) *Semin. Arthritis Rheum.* 11:151–71), local hypoxia, (Bengtsson, et al. (1986) *J. Am. Rheum. Assoc.* 29(7):817:21; Bennett, R. M. (1989) *J. Rheum.* (Suppl. 19) 16:185–91; Boessevain, M., (1991) *Pain* 45:227–38; Lund, et al. (1986) *Scand. J. Rheum.* 15:165–73; Simons, D. G. (1988) *Arch. Phys. Med. Rehabil.* 69:207–12) of sympathetic hyperactivity, (Bengtsson, A. and Henriksson, K. (1989) *J. Rheum.* (Suppl. 19) 16:144–9) but have not shown consistent abnormalities by light microscopy, histochemistry, or electron microscopy. Yunus, M. and Kalyan-Raman, U. P. (1989) *Rheum. Dis. Clin. North Am.* 15:115–34.

Needle electromyography (EMG) of painful muscle syndromes has produced variable results. The first was published by Buchtal and Clemmesen in 1940, (Buchtal, F., Clemmesen, S. (1940) *Acta. Med. Scand* 150:48–66), who concluded that the spontaneous EMG activity they identified arose in proprioceptive receptors. Since then a number of EMG studies have been performed on patients with lumbar disc disease (Elliott, F. A. 1944) *Lancet* 1:47–9), tension headache (Pozniak-Patewicz, E. (1976) *Headache* 4:261–6), fibrositis (Arroyo, P. (1966) *J. Florida Med. Assoc.* 53:29–31; Kraft, et al. (1968) *Arc. Phys. Med. Rehabil.* 49, I:155–62) fibromyalgia, (Durette, et al. (1991) *Am. J. Phys. Med. Rehabil.* 70,3:154–6; McBroom, et al. (1988) *Clin. J. Pain* 4:117–9; Zidar, et al. (1990) *Pain* 40:249–54) and myofascial taut bands (Dexter, J. R. and Simons, D. S. (1981) *Arch. Phys. Med. Rehabil.* 62:521–2; Friction, et al. (1985) *Arch. Phys. Med. Rehabil.* 66:314–16). High-frequency firing from TrPs has been described (Travell (1957) *Proc. Rudolf Virchow Med. Soc.* 16:128–36), but in the 1983 TrP Manual, Travell and Simons concluded that TrPs showed no resting activity and that any activity seen was either insertional or motor unit activity (Travell and Simons, supra). Intravenous regional sympathetic blockade with guanethidine also has been utilized. (Bengtsson and Bengtsson (1988) *Pain* 33: 161–167).

Several currently available treatment modalities or methods of treatment for chronic pain associated with myofascial trigger points have been described. One treatment of myofascial trigger points is local injection of the painful region, without localization of a neuromuscular abnormality, with local anesthetics including lidocaine, procaine and bupivacaine. Travell and Simons, supra; Sola, A. E. Trigger Point Therapy in Clinical Procedures in Emergency Medicine (Edited by J. R. Roberts and J. R. Hedges. Philadelphia, W. B. Saunders, 1985, pp 674–686). However, this treatment reportedly has only temporary effects. Also described is the transdermal delivery to a painful region of alpha-adrenergic blocking agents. Campbell, U.S. Pat. No. 5,070,084 and WO 92/14453. Dry-needling (inserting a needle into the trigger point without injecting anesthetic) is advocated (Gunn, CC, (1980) *Spine* 5(3):279) although injection of local anesthetic reportedly is more effective and less painful. (Cooper, A. L. (1961) *Arch. Phys. Med.* 43:704; Brav, E. A. and Sigmond, H. (1941) *Ann. Intern. Med.,* 15:840; Frost, F. A., et al. (1980) Lancet 1(3):499–501).

SUMMARY OF THE INVENTION

This application provides novel methods for identifying patients with chronic pain including those susceptible to treatment with sympathetic antagonists, and for so treating that pain. The treatment regimen may be used to block or inhibit pain, dysfunction and other referral phenomena that result from spontaneous EMG activity, as well as other pathology in trigger points and tender points.

Specifically, the method for treating chronic muscle pain involves directly contacting a neuromuscular abnormality with an amount of sympathetic antagonist sufficient to inhibit activity associated with that neuromuscular activity. The method for treating chronic muscle pain may also involve locating one or more myofascial trigger point by manual palpation, insertion of an EMG needle and detection of spontaneous EMG activity associated with the trigger point and contacting the trigger point with enough adrenergic antagonist to inhibit the spontaneous EMG activity. The method of identifying patients susceptible to treatment with sympathetic antagonists involves detecting a specific and localized activity associated with a neuromuscular activity. Such as: spontaneous EMG. Finally, the application provides a kit for identifying or treating chronic muscle pain.

DETAILED DESCRIPTION

Figure 1:
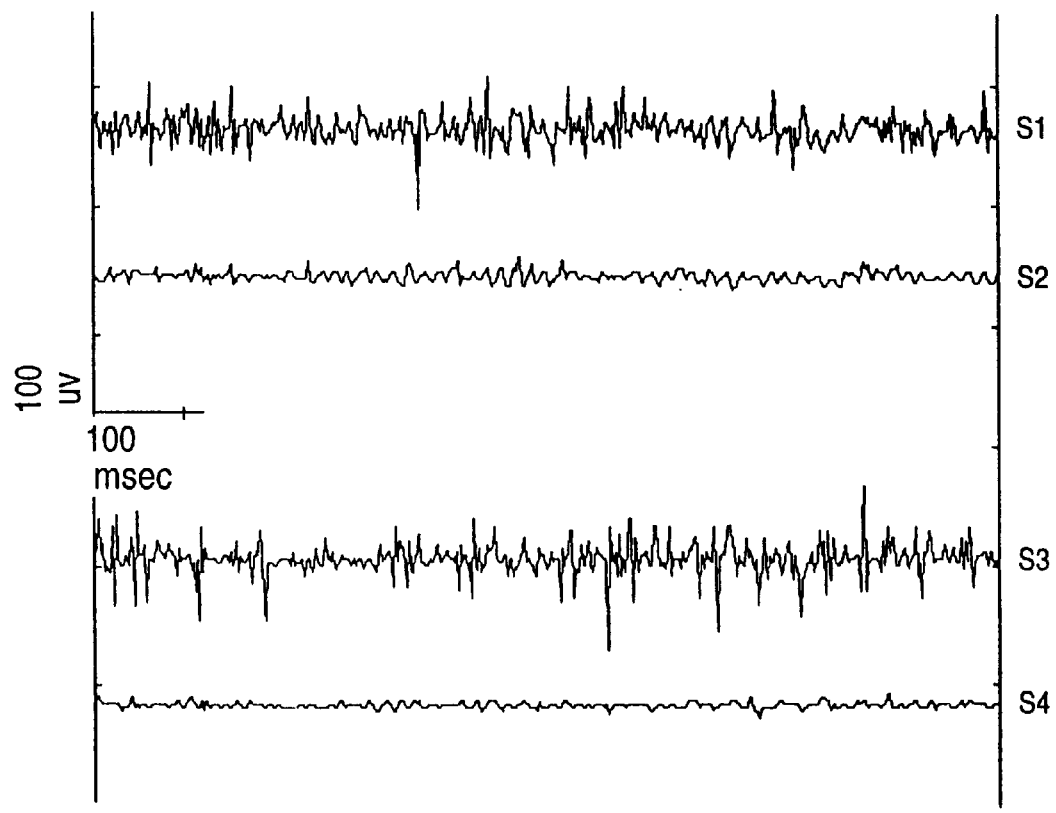
FIG. 1 shows an electromyograph recording of spontaneous EMG activity in two separate trapezius trigger points (S1 and S3) and in two separate non-tender sites (S2 and S4) adjacent these trigger points (1 cm away) in the same muscle. Data from two normal subjects are shown.

In accordance with the subject invention, methods are provided for identifying neuromuscular abnormalities which are the source of chronic muscle pain and for inhibiting or blocking chronic muscle pain in patients identified as potential treatment candidates.

This application provides novel methods for identifying patients with chronic pain susceptible to treatment with sympathetic antagonists, and for so treating that pain. The treatment regimen may be used to block or inhibit pain, dysfunction and other referral phenomena that result from spontaneous EMG activity, as well as other pathology in trigger points, tender points, or other neuromuscular abnormalities.

Specifically, the method for treating chronic muscle pain involves locally delivering a neuromuscular abnormality with an amount of sympathetic antagonist sufficient to inhibit activity associated with that neuromuscular activity. The abnormality may occur in muscles of the head, neck, extremity or back, and may be a sympathetically activated muscle spindle. The antagonist may be an adrenergic antagonist, more particularly phentolamine, phenoxybenzamine, or guanethidine.

The method for treating chronic muscle pain may also involve locating one or more myofascial trigger points by manual palpation, inserting of an EMG needle, detecting spontaneous EMG activity associated with the trigger point and directly contacting the trigger point with enough adrenergic antagonist to the trigger point to inhibit the spontaneous EMG activity.

The method of identifying patients susceptible to treatment with sympathetic antagonists involves detecting a specific and localized activity associated with a neuromuscular activity. The method also may involve locating a neuromuscular abnormality having spontaneous EMG activity and directly contacting that abnormality with an amount of reversible sympathetic antagonist sufficient to inhibit spontaneous EMG activity. If contacting the abnormality with the antagonist reduced spontaneous EMG activity, then the patient is susceptible to treatment. The antagonist may be an alpha adrenergic antagonist, more particularly phentolamine, still more particularly 10 to 100 mg of phentolamine.

Finally, the application provides a kit for identifying or treating chronic muscle pain.

The subject invention offers several advantages over currently available methods for identifying and treating chronic muscle pain. The method of identifying spontaneous EMG activity in neuromuscular abnormalities such as TrPs both identifies the source of pain and provides information as to which patients are most likely to benefit from localized treatment, including with agents which antagonize sympathetic transmission. Neuromuscular abnormalities may be associated with symptoms such as spontaneous TrP EMG activity, activation of TrP EMG by stressors, and deactivation by sympathetic blockers. This activity may be correlated with symptoms such as referred pain to the ipsilateral cervical, occipital and/or temporal area, and can be used as a means of (1) screening patients for those most likely to benefit from therapy and (2) identifying the neuromuscular abnormalities which are associated with a clinical pain syndrome. Additionally, the identification of the spontaneous electrical activity associated with neuromuscular abnormalities allows use of agents which can specifically treat the pharmacological basis of the pain on a long term basis.

The subject invention advantageously provides a method of obtaining a long-lasting (e.g. 4 months or more) or even permanent pharmacologic blockade of pain and related symptoms associated with neuromuscular abnormalities. Such treatment eliminates the need for repeated treatments, such as repeated dry needling of the site or regional injection of agents such as lidocaine and procaine. The long-term duration of relief results from the direct delivery to a neuromuscular abnormality. Because the delivery is localized rather than systemic, undesirable side effects such as postural hypotension, dizziness, fatigue and other common cardiovascular events are3 minimized or eliminated. Localized delivery also permits delivery of dosages that might cause severe harm if delivered systemically.

The method for identifying neuromuscular abnormalities may include the steps of manual palpation using criteria which include the following: (1) palpable firmness of the muscle, (2) tenderness to palpation, (3) typical referral pattern of pain, and when present, (4) palpable local twitch response (Travell, J. and Simons, D. supra, pages 13–17); examining the identified TrPs or TePs, preferably by needle EMG; determining whether the TrP or TeP is active; and determining the precise location of the TrP or TeP. If spontaneous electrical spike activity is present, the agent(s) which inhibit or block sympathetic transmission are injected directly into the neuromuscular abnormality. Spontaneous activity is defined as localized electrical activity recorded from a muscle or a nerve at rest after insertional activity has subsided, in the absence of voluntary contraction or external stimulus. The screening and treatment methods involve localized delivery of one or more agents and the subsequent observation of reduced or eliminated spontaneous activity resulting from the delivery of the agent.

Neuromuscular abnormalities include trigger points (TrPs) which comprise sympathetically-activated muscle spindles, tender points (TePs), areas of tender muscle and the like. The neuromuscular abnormalities may be associated with several types of muscle or nerve activity, including spontaneous EMG activity, sympathetic activity and abnormal muscle or nerve activity. It is a theory of the invention that in the neuromuscular abnormality, the needle EMG activity arises from the intrafusal muscle fiber contractions and that, as a result, pain arises from the spindle capsule, which is distended and under pressure. Chronic muscle pain is characterized by symptoms which may include chronic pain and muscle dysfunction. The principal muscle dysfunction is stiffness, decreased flexibility and decreased range of motion. In addition, muscle pain is increased by overexertion, forceful contraction and prolonged immobilization.

The compositions used in the screening and treatment methodologies of the subject invention include one or more agents which antagonize or block sympathetic transmission and/or function of the affected spindle. Such agents include (i) sympathetic blocking agents which bind to alpha adrenergic receptors and (ii) agents which deplete transmitters. The blocking agents may be reversible alpha receptor antagonists such as phentolamine, tolazoline, prazosin, terzosin, doxazosin, trimazosin, and indoramin or irreversible alpha receptor antagonists such as phenoxybenzamine or dibenzamine. Agents which are depletors of transmitters include guanethidine, guanadrel, reserpine, or metyrosine.

TrPs are identified in patients with chronic pain by finger palpation for localized (1–3 cm diameter) muscle firmness ("taut band"), tenderness to steady pressure with the thumb or first two fingers and referral of pain in characteristic patterns as described by Simons and Travell, supra. Patients are asked to rate their level of pain prior to as well as during testing. It is important to locate precisely the appropriate neuromuscular abnormality(ies) and to confirm that they are, for example, active TrP(s) associated with a chronic pain syndrome. Typically, a patient may have two or more TrPs in a given area such as the shoulder or low back. If no neuromuscular abnormality can be found which reproduces or aggravates the patient's complaints of pain, the procedure of injecting agents which inhibit the block sympathetic transmission is not performed. Only patients with a combination of pain and a related neuromuscular abnormality should be treated by inhibition or blockade of spontaneous electrical activity.

Following manual identification of the neuromuscular abnormality, the affected spindle is sought by needle EMG and EMG activity is determined. This is accomplished by comparing the needle EMG activity in the TrPs identified by manual palpation with the EMG activity in adjacent non-tender fibers (control) of the same muscle. To detect the TrP EMG activity, at least one needle is inserted into the muscle having the neuromuscular abnormality. More preferably, at least two needles are inserted. One needle is inserted in the putative neuromuscular abnormality which was previously localized by palpation or other suitable method. A second needle is inserted in an adjacent non-tender fiber which elicits substantially no electrical signal, as a control and reference for activity which may be detected with the first needle. Generally monopolar disposable needles are used to reduce the risk of infection. Additionally, monopolar needles record from a wider area than concentric bipolar needles, a feature which is helpful in demonstrating that areas adjacent to the trigger points are substantially electrically quiet. All needles inserted may be referenced to an equidistant surface electrode.

The control EMG activity in the non-tender fibers should be substantially electrically silent and elicit no pain. In general the TrP EMG should be $\geq 40$ $\mu V$ amplitude and can be 500 $\mu V$ or greater. The adjacent muscle should be less than 20 $\mu V$ amplitude. During the procedure the relative difference between the two recordings is viewed visually on an oscilloscope, or by digital area-under-the-curve or root mean square on-line calculation. The TrP is selected for local delivery of a therapeutic agent when the TrP exhibits a mean EMG amplitude which is about 20 $\mu V$, preferably about 40 $\mu V$, more preferably about 100 $\mu V$ greater than the control EMG amplitude. On average, latent TrPs do not display a mean EMG amplitude of less than 10 $\mu V$ or greater than 40 $\mu V$.

The affected spindle EMG activity may be pinpointed by moving the EMG needle inserted in the neuromuscular abnormality in small (about 1 mm) increments until the patient reports experiencing the same pain and referral pattern as was experienced during, for example, manual palpation, to identify the neuromuscular abnormality. The EMG needle can be withdrawn and inserted until the precise location of the neuromuscular abnormality is identified. Once the neuromuscular abnormality in the muscle is identified precisely, a hypodermic needle is inserted beside the first needle and advanced to the same depth. The neuromuscular abnormality will generally be located one half inch to three inches below the skin surface, and most typically will be approximately one and one half inch below the skin surface. The neuromuscular abnormality is then contacted directly with an agent which inhibits or blocks sympathetic activity, such as an alpha adrenergic antagonist, in an amount sufficient to block the spontaneous EMG activity and, as a result, inhibit or block the pain associated with the EMG activity in the neuromuscular abnormality. When there are several neuromuscular abnormalities that meet the criteria indicated above, it may be necessary to inject each.

Any of a variety of agents which inhibit or block sympathetic or spindle activity can be used. Preferred agents are alpha adrenergic antagonists. Temporary relief can be obtained using transient (reversible) alpha adrenergic antagonists such as phentolamine. Effective dosages may range from at least about 2 mg to 100 mg, usually 10 mg. Such agents can also be used as a means of screening candidate patients to confirm the potential efficacy of using irreversible agents such as phenoxybenzamine or guanethidine as a means for treating a particular patient.

The preferred agent for treatment of chronic muscle pain is phenoxybenzamine hydrochloride, also known by the trademark name "Dibenzyline" (SmithKline Beecham Pharmaceuticals). Oral dibenzyline has a labelled indication for use in control of episodes of hypertension and sweating in patients with pheochromocytoma. It has not previously been employed in treatment of chronic muscle pain. Dibenzyline should generally be prepared according to the manufacturer's instructions. However, contrary to the manufacturer's instructions, it is given intramuscularly rather than orally. The volume of injection may vary from at least 0.1 cc to 2.0 cc, usually about 0.5 cc. Effective dosages may range from at least about 1 mg to 50 mg, usually 5–10 mg. There may be some local muscle irritation at the site of intramuscular injection or other means of localized delivery.

Another sympathetic antagonistic agent of interest is guanethidine, also known by the trademark name "Ismelin" (CIBA-GEIGY). Ismelin should generally be prepared according to the manufacturer's instruction. Effective dosages may range from at least about 10 mg to 100 mg, usually 25 mg. The pH may be adjusted to decrease tissue irritation, for example a pH of 8. The drug is then administered intramuscularly rather than intravenously as instructed by the manufacturer.

The sympathetic antagonists may be used either alone or in combination with other antagonists. These agents may decrease local tenderness or enhance the effect of the sympathetic antagonist. Examples of these agents are lidocaine and prednisone.

Sympathetic antagonists may be formulated and used according to the manufacturer's directions. Alternatively, the compound may be reformulated in a composition specifically designed for localized intramuscular or intraspindle administration. For example, the composition may be designed to reduce or even eliminate localized pain and irritation, for example by eliminating propylene glycol and ethanol from the formulation of phenoxybenzamine hydrochloride, or by encapsulating phenoxybenzamine hydrochloride in, e.g., liposomes, emulsions, micelles, a gel such as hydroxycellulose, or time-release formulation. Also, such compositions may be formulated to optimize intraspindle delivery. Such a formulation might take advantage of the high concentration of hyaluronic acid within the spindle, for example, by utilizing hyaluronic acid or other suitable mucopolysaccharide, or hyaluronidase. The adrenergic antagonist might also be conjugated to or formulated with a compound that selectively targets hyaluronidase.

The spike activity in the first needle is essentially eliminated within 2–5 minutes of delivery of the adrenergic antagonist, making it virtually indistinguishable for the adjacent needle activity. Have a localized pain as a result of injection may be experienced and the site may remain sore for as long as a week. When irreversible agents are used, pain reduction is significant at 1 month and still at 4 months. The localized delivery of these agents reduces or eliminates undesirable side effects commonly associated with the systemic administration of such compounds, including for example dizziness, postural hypotension, or fatigue.

Pain relief usually is reported after the first treatment. Patients having multiple neuromuscular dysfunctions may receive multiple injections either at the same treatment session or in several treatment sessions. Once treated, a trigger point generally does not require treatment again, but it would not be unexpected for re-treatment to be necessary in 6–12 months from the initial treatment.

Following administration of the therapeutic agent(s), patients record their pain observations in a pain diary or some other means for recording pain perceptions. The patient may return to the clinic for assessment of the response to treatment. If spontaneous EMG activity is subsequently monitored, it may also be observed to decrease. If there has been no response to the initial treatment, then additional treatments generally are not recommended. Responsive patients receiving long-acting agents may expect partial to complete pain relief and recovery of muscle function for about 3 to 12 months, and often pain will not recur.

The subject compositions can be provided as kits for use in screening or treatment of patients and/or for one or more treatments. The kits may comprise: (1) disposable sterile EMG needles, preferably monopolar or multi-port needles; (2) a hypodermic syringe; and (3) a container of an appropriate agent, which may be further diluted prior to use or provided at the concentration of use. The containers may include one or more dosages. For screening, a reversible sympathetic antagonist agent, e.g., phentolamine, is appropriate. For treatment, an appropriate irreversible agent, e.g., phenoxybenzamine or guanethidine, may be preferred. Conveniently, single dosages may be provided in syringes, contained in sterilized containers, so that the physician may employ the syringes directly, where the syringes will have the desired amount and concentration of agents.

When desired, the container having the sympathetic antagonist agent may also contain agents which may be administered in combination with the sympathetic antagonist agent, such as lidocaine or prednisone. Where a combination of agents is employed, these agents are present in the containers in the desired proportional amounts. Thus, the kit may have a plurality of syringes containing a sympathetic antagonistic agent of choice in amounts appropriate for screening and/or for therapy. Where the syringes contain the formulation for direct use, usually there will be no need for other reagents for use with the method.

The subject methods and compositions find use in the diagnosis and treatment of chronic muscle pain associated with neuromuscular abnormalities such as myofascial trigger points, tender points, sympathetically activated muscle spindles and the like. Chronic muscle pain syndromes which may be amenable to the method of treatment of the subject invention may include fibromyalgia, myofascial pain syndrome, tension headache, temporomandibular joint dysfunction (TMD), neck and low back pain syndromes and the like. The methods and compositions may also be used as a means of screening for patients who may benefit from treatment, particularly by evaluating the efficacy of reversible antagonists such as phentolamine in blocking pain, dysfunction and/or spontaneous EMG activity in neuromuscular abnormalities.

The following examples are offered by way of illustration and not by way of limitation.

EXAMPLES

Patients presenting to the Neurologic Centre for Headache and Pain with TrPs on physical examination and who agreed to undergo needle EMG were studied. Procedures followed were in accord with the standards for human experimentation. Informed consent was obtained after the nature of the procedure had been fully explained to each subject.

Example 1

Method of Identifying Myofascial Trigger Points by Demonstration of Spontaneous Needle EMG Activity This study was undertaken to correlate spontaneous electrical activity with the existence of myofascial trigger points in patients exhibiting chronic muscle pain. For all subjects and patients, ages ranged from 18 to 80, mean 38.6, mode 36. Eighty percent of these subjects were women. The patient group examined included twenty-nine patients with chronic tension-type headache accompanied by pericranial muscle tenderness as diagnosed by a board-certified neurologist according to the criteria of the International Headache Society (International Headache Society, Headache Classification Committee: Classification and diagnostic criteria for headache disorders). These headache patients had mild to moderate daily normal neurologic examinations except for the presence of TrPs. Twenty-five patients meeting the American College of Rheumatology criteria for fibromyalgia (Wolfe, F., et al. (1990) *Arthritis Rheum.* 33,2:160–72) had mild to moderate daily fluctuating bilateral neck or shoulder and low-back or buttock pain. These fibromyalgia patients also had normal neurologic examinations except for the presence of TrPs. No patients had myopathies, neuropathies, radiculopathies or other significant medical disorders.

Eight normal subjects were also examined. Normal patients had no history of significant head, neck, or back pain but did present with latent TrPs as identified by palpatory examination. Normal subjects with latent TrPs were chosen so that needle placement in a TrP could be compared with a needle placement in non-TrP muscle fibers.

TrPs were identified by finger palpation for localized (1–3 cm diameter) muscle firmness ("taut band"), tenderness to steady pressure with the thumb or first two fingers, and referral of pain in characteristic patterns as described by Simon and Travell (Travell, supra). TrPs in the upper trapezius were chosen for needle EMG examination because these could be identified in all patients, regardless of site of pain, and in all normal subjects (latent TrPs). The tenderness rating of the TrPs when steady pressure is applied is as follows: 0, no tenderness; 1, mild tenderness without grimace or flinch; 2, moderate tenderness plus grimace or flinch; 3, severe tenderness plus marked flinch or withdrawal; 4, unbearable tenderness (patient withdraws with light touch). Patients were also asked to rate their level of pain before testing, according to the following scale: 0, no pain; 1, ignorable pain; 2, moderate pain; 3, pain that interferes with one's activity; 4, incapacitating pain requiring bed rest or cessation of activity.

Monopolar TECA disposable EMG needles were inserted through the skin directly over the TrPs. A second needle was placed 1 cm away in non-tender fibers of the same muscle. Both needles were referenced to the same equidistant surface electrode. High and low cuts were 10,000 and 30 Hz, gain was 100 $\mu$V per division, sweep speed was 100 milliseconds per division, displayed on a 2-channel Cadwell Quantum 84 machine (Kennewick, Washington). After ascertaining that the second site (negative control) was substantially electrically silent and elicited no pain (hereafter called the non-TrP), the Trp needle was advanced in 1-mm increments until the subject reported experiencing the same pain and referral pattern experienced during manual palpation. The site at which this occurred was diagnosed as the TrP. Typically, the subject reported pain simulating that experienced during manual palpation at a depth of about 2 cm, with the patient or subject reporting a deep steady ache or squeezing sensation that radiated to the ipsilateral cervical, occipital or temporal areas as described by Travell and Simons. (Travell, supra). If necessary, the needle was withdrawn and redirected until the precise point could be identified. Once the precise TrP was contacted, The EMG needles were left in place for 15–50 minutes.

All EMGs were saved on disc and printed. The Cadwell Quantum 84 Area software was used to calculate the absolute (both negative and positive deflections from the baseline) area-under-the-curve and the mean amplitude for each I-second interval (the full screen width at a sweep of 100 msec). EMG activity recorded at the non-TrP site served as the baseline.

Figure 2:
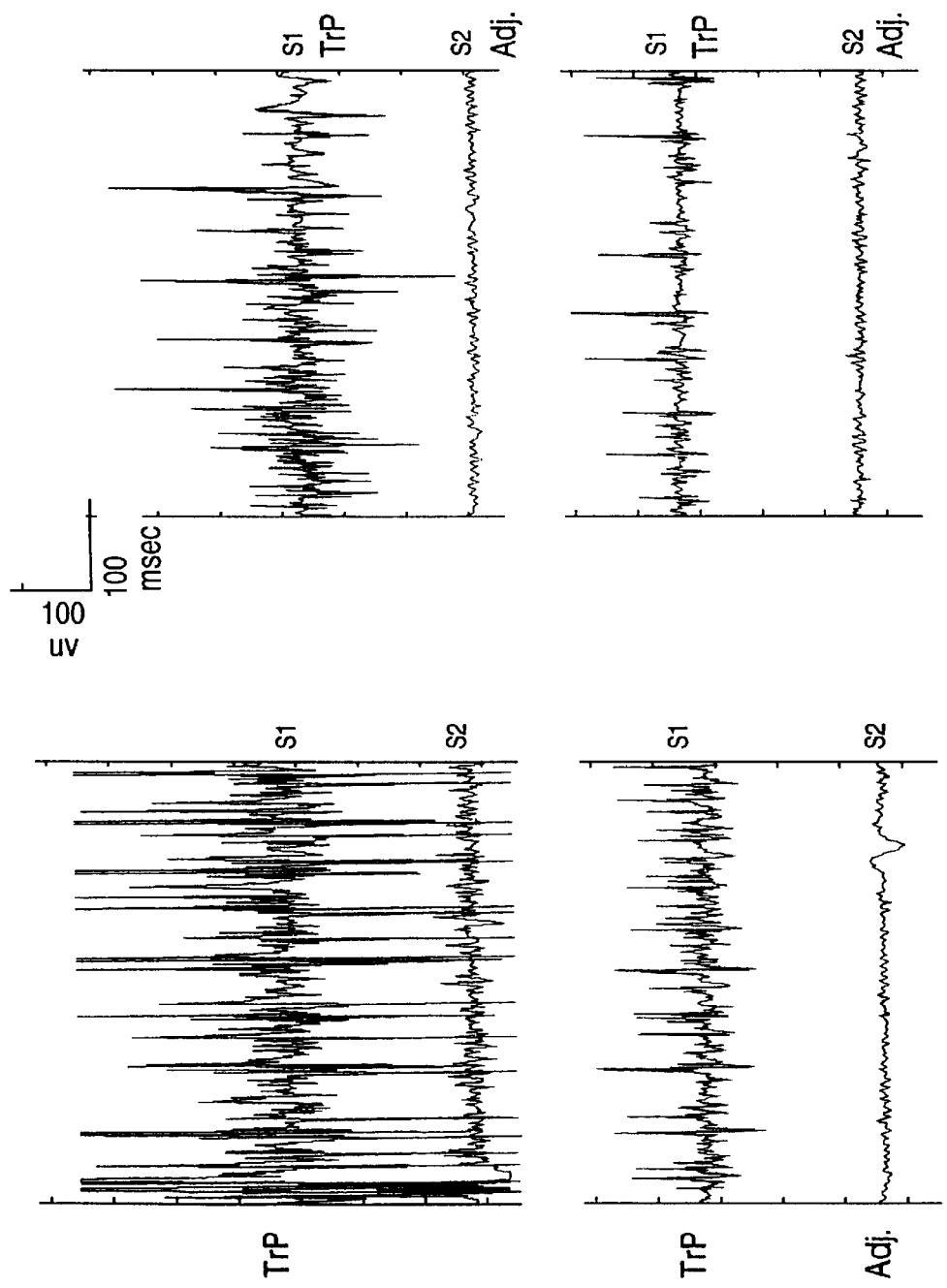
FIG. 2 shows an electromyograph recording of spontaneous EMG activity in a trapezius trigger point (S1) and an adjacent non-tender site 1 cm away in the same muscle (S2). Data from four patients are shown.

No fibrillation potentials or positive sharp waves were seen in any normal subjects or patients. Brief insertional activity could be seen when the needle was first inserted or the subject moved, in which cases both the TrP and the non-TrP needles recorded typical motor unit potentials. These typical motor unit potentials either disappeared spontaneously or could be readily eliminated by relaxing the muscle. Spontaneous EMG activity was recorded from the TrPs of all normal subjects and patients. The EMG activity disappeared when the TrP needle was moved by as little as 1 mm. No spontaneous activity was recorded from Non-TrPs. In all normal subjects and patients, the appearance of the spontaneous EMG activity corresponded to the report of pain. The pain was described as a deep aching or squeezing sensation, typically associated with a referral of pain upward into the cervical, occipital, or temporal areas, and often associated with autonomic symptoms such as light-headedness, diaphoresis, or nausea. The spontaneous activity was present for as long as the needle remained in place, up to 50 minutes in some instances. Examples of spontaneous EMG activity recorded in trapezius TrPs are presented in FIGS. 1 and 2.

Figure 3:
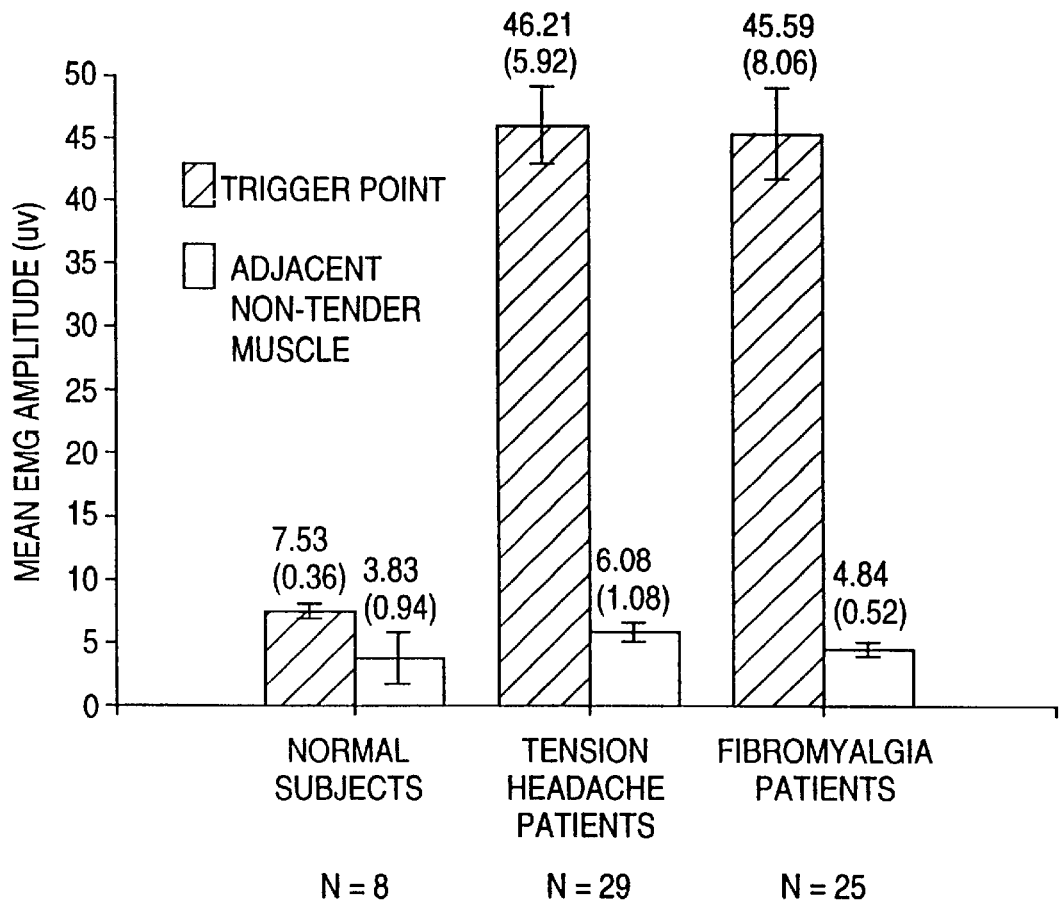
FIG. 3 is a graph showing the mean and standard errors for mean EMG amplitudes for the TrPs and adjacent non-TrPs in the trapezius of normal subjects having latent TrPs and in the trapezius of patient groups having active TrPs which produce symptoms of either tension headache or fibromyalgia.

FIG. 3 shows the means and standard error for mean EMG amplitudes for the TrPs and adjacent non-TrPs in the trapezius of normal subjects (latent TrPs) and patient groups (active TrPs). Because unequal sample sizes can exacerbate violation of statistical assumptions, both parametric and non-parametric analyses were performed. With either method of analysis, the TrP mean EMG amplitudes for normal subjects were significantly lower than for the two clinical groups. However, the mean EMG amplitudes of the two clinical groups were not significantly different from each other; in fact, the distributions were non-overlapping. No normal subject had a mean EMG amplitude greater than 10 $\mu$V, while no patient had a mean EMG amplitude less than 10 $\mu$V.

Pearson correlations between mean EMG amplitude and either age, self-reported pain or tenderness to palpation, as well as Point Biserial correlations between mean EMG amplitude and gender, were calculated. The correlations were as follows:

TABLE 1

| | Mean EMG Amplitude and Correlation | Significance of Correlation |
|---|---|---|
| Age | r(62) = 0.07 | NS* |
| Gender | r(62) = 0.12 | NS |
| Pain | r(59) = 0.14 | NS |
| Tenderness | r(58) = 0.43 | Significant at p = 0.0007 |

*NS = not significant

Thus, mean EMG amplitude was significantly correlated with tenderness to palpation of the TrP, but not with self-reported pain, age, or gender.

Spontaneous EMG activity was found in the 1–2 mm nidus of myofascial TrPs. The activity disappeared if the recording needle was advanced or withdrawn as little as 1 mm. When the needle reached the TrP, the patients consistently reported the onset or aggravation of pain and the characteristic referral pattern of pain. This activity was sustained for as long as the needle was in place, up to a maximum recording period of 50 minutes. The second monopolar needle 1 cm distant showed no spontaneous activity. This provides further evidence that the TrP activity was limited to the small area identified and that motor unit activity was not occurring in adjacent muscle fibers. The TrP EMG mean amplitudes were significantly greater in the two groups of muscle pain patients than in normals. There was no significant difference between the muscle tension headache patients and the fibromyalgia patients.

This study demonstrated that spontaneous EMG activity correlated to TrPs, and facilitated precise localization of the TrP. The TrP, in turn, is associated with clinical manifestations of chronic pain. Thus, detection of localized spontaneous EMG activity associated with TrPs provides one method for identifying the precise source or cause of chronic pain.

Example 2

Correlation of Myofascial Trigger Point Needle EMG Activity With Autonomic Innervation The purpose of this study was to provide evidence of the role of the sympathetic innervation of muscle, and specifically to correlate that innervation with spontaneous electrical activity of TrPs that are associated with chronic pain. Psychological stress or conditions were used to alter autonomic activity levels and to correlate that activity with the resultant increase in spontaneous electrical activity of the TrP. Monopolar EMG needles were placed in TrPs and non-Trps identified as described in Example 1. Monopolar needle and EMG was simultaneously recorded from trapezius TrPs and non-TrPs in 14 normal male and female subjects, ages 20–44, during the following conditions: baseline activity at rest (B1), forward counting (FC), recovery baseline (B2), mental arithmetic stressor (MS), and recovery baseline (B3).

A J & J Enterprises (Poulsbo, WA) model T-68 electrodermograph with a preamp module, Ig-3, was used to collect electrodermal response data (skin conductance was measured in micro-mhos). Ag—Ag/Cl electrodes with a small coating of gel (Signa Gel, Parker Labs) were used. Electrodermal response was measured at the same time as EMG activity, and the response represented the average level of micromhos during each condition. This measure was used to infer generalized autonomic arousal in the stressful conditions.

A 16.5 cam visual analogue scale with anchors "not at all stressed" and "extremely stressed" was used to determine subjective stress level. The subject was asked to sit quietly and relax for at least for 5 min or until a stable baseline was obtained. After the adaptation period, a 5-s sample of EMG activity and electrodermal levels was recorded. Another sample was recorded 30 s later. This was the baseline task condition.

Subjects then were asked to count forward by ones for 120 s. This constituted the forward counting (i.e., control) task condition. EMG and electrodermal activity were recorded for 5-s epochs at 10, 45, and 115 s into the task. Subjects then sat quietly until EMG activity returned to approximately baseline levels (typically, 2 min). Then a 5-s sample of EMG and electrodermal activity was recorded. This period was defined as the rest interval task condition.

Next, a mental arithmetic exercise was used to induce stress in the subjects. This type of stressor has been used in many previous investigations (Anderson & Franks, 1981); Andrasik, Blanchard, Arena, Saunders, & Barron, 1982; Feuerstein, Bush, & Corbisiero, 1982; Gannon, Haynes, Safranek, & Hamilton, 1981). Subjects were asked to count backward aloud by sevens or thirteens, starting with 902. They were asked to subtract as quickly as they could. The researcher pressured the subjects to go faster during the procedure and corrected subjects when they made mistakes. Subjects performed the mental arthrimetic for 120 s. Again, EMG and electrodermal activity were recorded for 5-s epochs at 10, 45, and 115 s into the task. This period constituted the backward counting (i.e., stress) task condition.

After the backward counting task, subjects sat quietly until the EMG activity returned to approximately the pretest level (typically, 2 min). A 5-s sample of EMG and electrodermal activity was recorded. Another sample was recorded 30 s later. This was defined as the recovery task condition. After the last recovery task condition, the needles and skin conductance sensors were removed, and each subject completed the self-report visual analogue scale.

To validate the stress task condition (backward counting), both subjective stress ratings and skin conductance levels were analyzed. Visual analogue ratings were significantly higher during the backward counting condition than the non-stress conditions, t(13)=4.9, p<0.001. Although skin conductance levels remained high throughout the experimental procedure (overall level: M=20.23, SD=8.77; pre-EMG: M=12.56, SD=5.77; baseline: M=20.97, SD=8.28; forward counting: M=21.04, SD=9,14; backward counting: M=24.65, SD=10.06; recovery: M=22.10, SD=9.83), skin conductance during the backward counting condition was significantly greater than all other conditions, t(13)=3.69, p=0.003.

Figure 4:
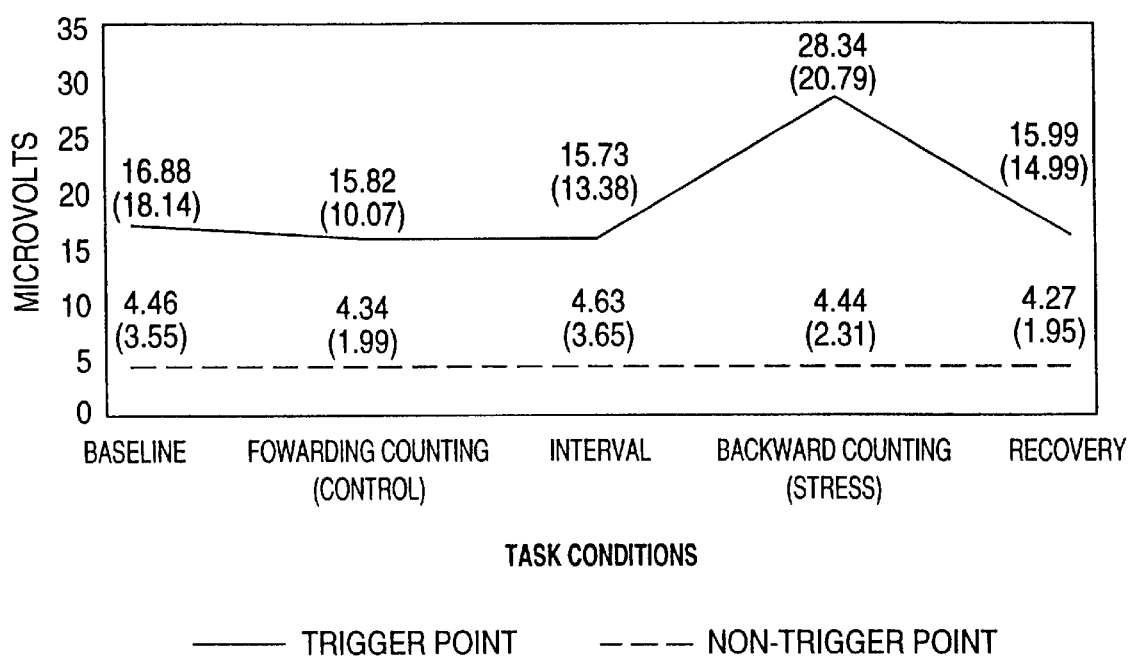
FIG. 4 is a graph showing the means (standard deviations) of mean amplitude EMG activity for trigger point and non-trigger point muscle across task conditions.

To test the differential response between the trigger point and the non-trigger point muscle, a two-way analysis of variance (ANOVA) with two repeated measures was used. The means and standard deviations for each of the conditions and sites are shown in FIG. 4. Violations of the sphericity assumption were managed through the use of the Huynh-Feldt correction. Thus, all probability levels are reported with the appropriate correction.

The interaction between site (trigger point vs. non-trigger point) and conditions (baseline, forward counting, rest interval, backward counting, and recovery) was significant, F (4,52)=5.901, p=0.01 ∈=0.4377. There were significant main effects, F(1,13)=15.429, p=0.002, between trigger point (M=18.55, SD=16.22) and non-trigger point (M=4.43, SD=2.72) EMG activity, and between the task conditions, F(4,52)=6.610, p=0.003 ∈=0.5684.

The results are shown in the Table below.

TABLE 2

| | Mean EMG Amplitudes (means/s.d in microvolts) | | | | |
|---|---|---|---|---|---|
| | B1 | FC | B2 | MS | B3 |
| TrP | 16.9/18.1 | 15.8/10.1 | 15.7/13.4 | 28.3/20.8 | 16.0/15.0 |
| Non-TrP | 4.5/3.6 | 4.3/2.0 | 4.6/3.7 | 4.4/2.3 | 4.3/2.0 |

The t-test results in this study revealed that the trigger point EMG activity was significantly greater than the non-trigger point EMG activity during each task condition (baseline: t=2.64, p=0.02; forward counting: t=4.59, p<0.001; interval: t=2.84, p=0.02; backward counting: t=4.33, p<0.001; recovery: t=3.04, p=0.009).

A one-way ANOVA was calculated for trigger point EMG recordings among the non-stress task (i.e., baseline, forward counting, rest interval, and recovery). The results of the ANOVAs were not significant, F(3,39)=0.142, p=0.085, ∈=0.5993. Another paired-differences t test compared the combined trigger point EMG response for the non-stress tasks (baseline interval, forward counting, and recovery) with the trigger point EMG response during the backward counting (stress) task. The test revealed a significant difference, t(1,13)=3.104, p=0.008, between the non-stress trigger point (M=16.12, SD=13.71) and the stress trigger point (M=28.34, SD=20.79) EMG activity. Only the stress task significantly increased the EMG activity level for the trigger points.

Pearson correlations were computed between the trigger point and non-trigger point EMG recordings at each of the task conditions. None of these correlations was significant (base-line: r=0.24, forward counting: r=0.44, interval: r=0.35, backward counting; r=0.11, recovery: r=0.35).

As was seen in the previous study, EMG activity was significantly greater in TrPs than in non-TrPs in all conditions. In the stress condition, the TrP EMG activity showed a significant increase when compared to all non-stress conditions. Non-TrP EMG activity showed no change. Thus, a mental stressor increased TrP EMG activity without increased motor unit activity in adjacent muscle fiber areas.

These results are consistent with the theory that TrP EMG activity, which has been correlated to chronic pain conditions, arises in intrafusal muscle fibers which are sympathetically activated. Thus, the study suggests that eradication of the sympathetic activation of the TrP may provide a therapy for the chronic muscle pains associated with those TrPs.

Example 3

Method of Inhibiting Spontaneous TrP Electrical Activity With Phentolamine

The purpose of this study was to investigate whether chronic muscle pain could be treated by inhibiting spontaneous electrical activity associated with sympathetic innervation of TrPs by injection of a sympathetic antagonist. Phentolamine was chosen for this study because of its temporary inhibitory effect. A first group of subjects with myofascial trigger point pain syndromes were evaluated and the location of their TrPs determined as described in Example 1.

Seven patients received 5 to 10 mg phentolamine injected directly into TrP. Local injection of phentolamine was performed in 4 normal subjects with latent trigger points and 3 patients with tension headaches associated with active trigger points in the trapezium. The normal subjects included two men, ages 27 and 43, and two women, ages 28 and 40. The muscle tension headache patients were two women, 28 and 51, and one man, 36. None were taking preventative medications, and none had taken any medication including analgesics within 3 days. None had other medical problems.

Figure 5:
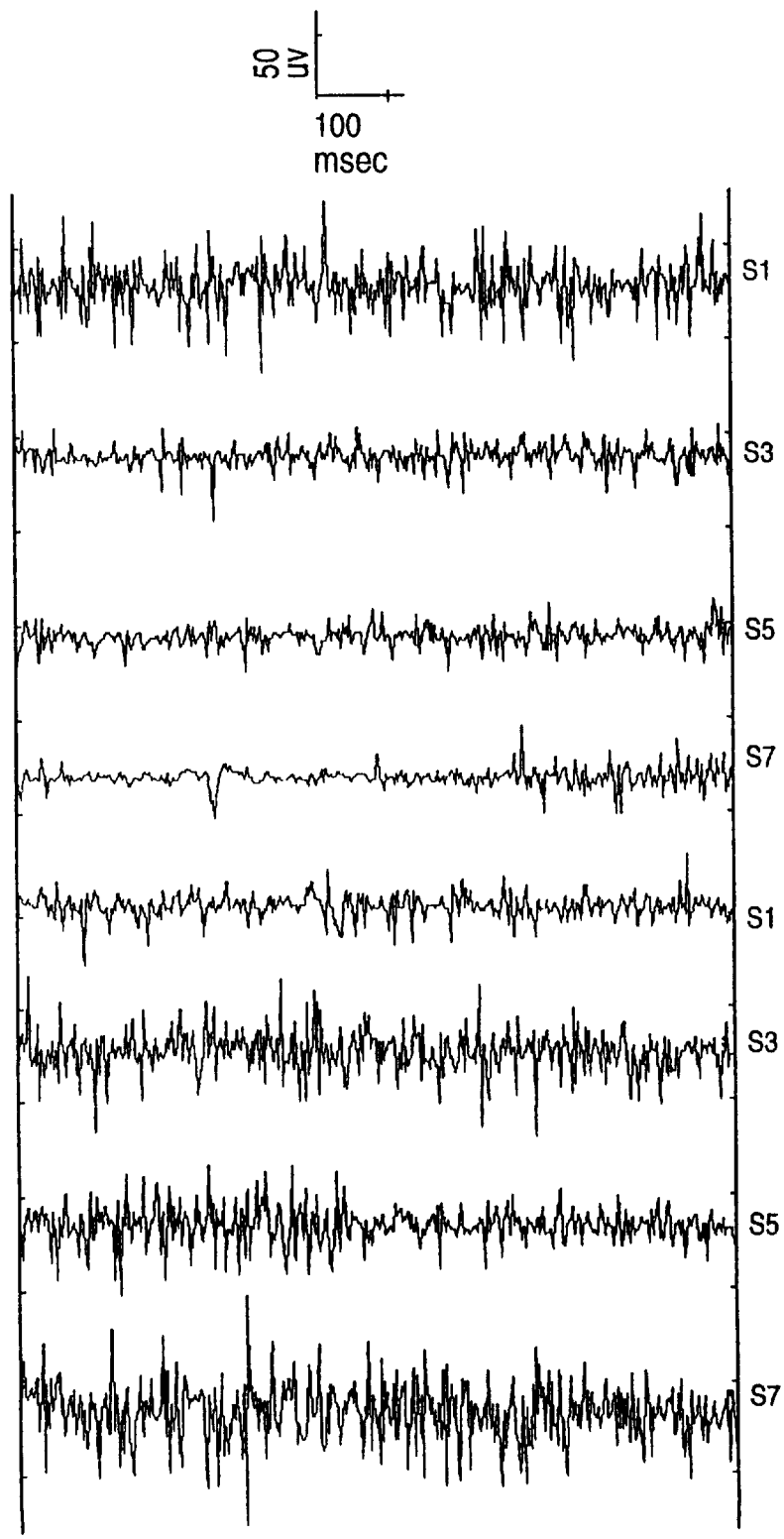
FIG. 5 is an electromyograph recording showing the progressive reduction and return of trigger point activity in a normal subject. The top tracing is prior to phentolamine injection and each subsequent tracing is at 5-minute intervals after injection.
Figure 6:
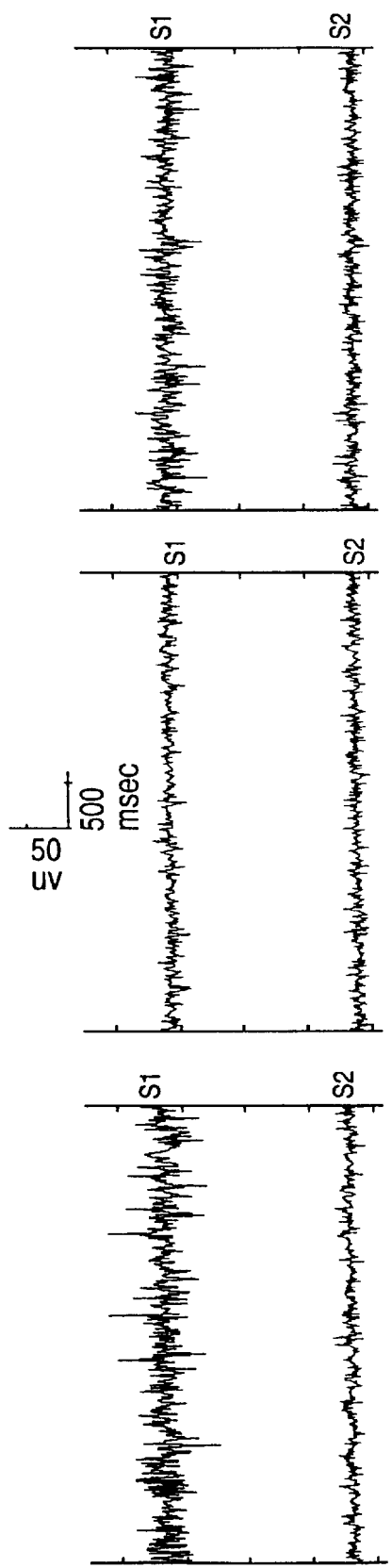
FIG. 6 is an electromyograph recording showing the trigger point EMG changes in a normal subject. The left frame shows the trigger point and non-tender EMG activity before phentolamine. At 20 minutes after sympathetic blockade (middle frame) the trigger point EMG activity is virtually indistinguishable from the adjacent non-tender site activity. At 40 minutes (right frame) the trigger point activity has partially returned.
Figure 7:
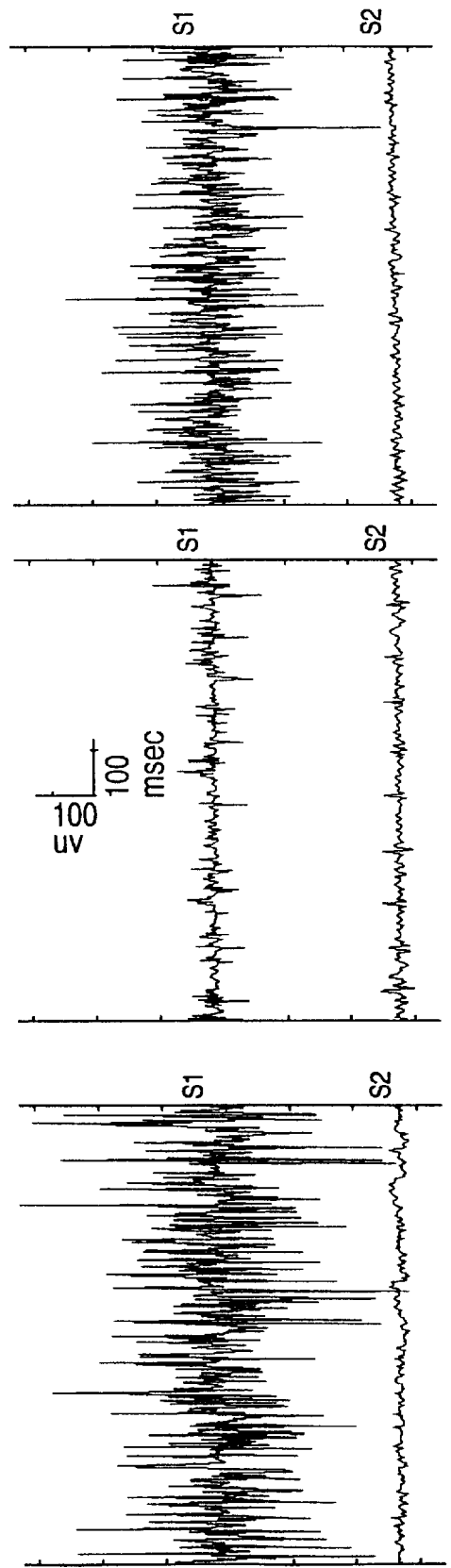
FIG. 7 is an electromyograph recording showing the phentolamine responses from a chronic tension headache patient.
Figure 8:
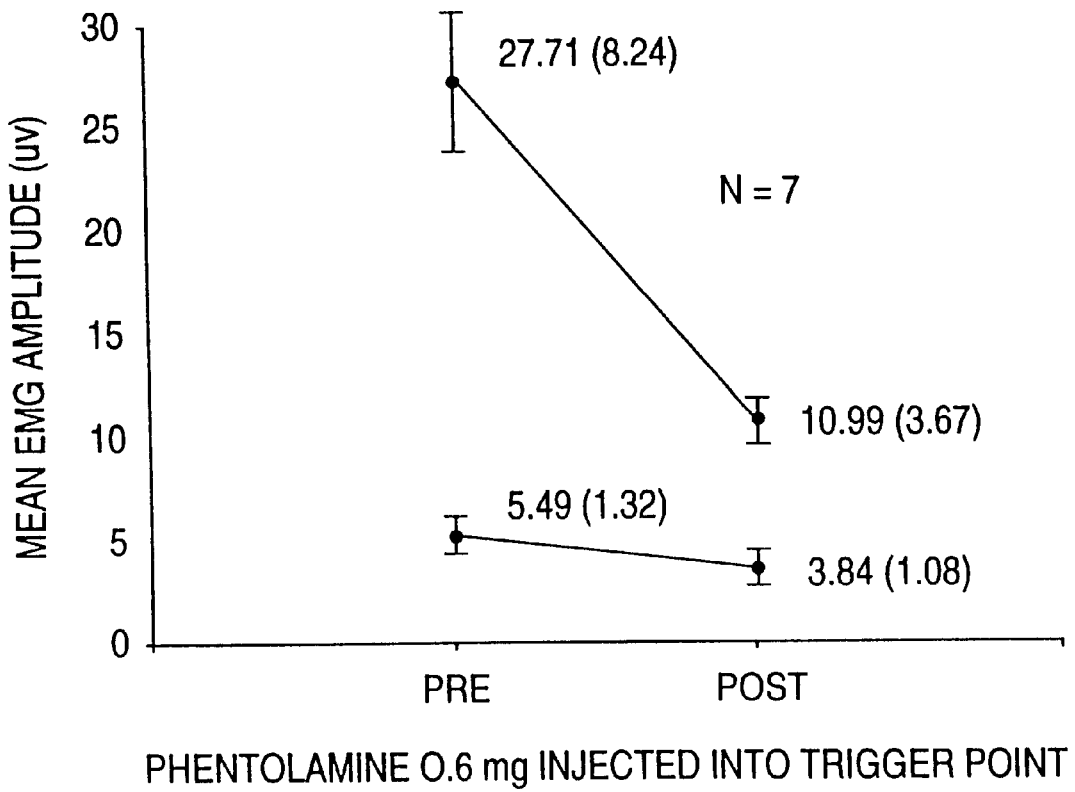
FIG. 8 is a graph showing the mean and s.d. of mean EMG amplitude before and 5 minutes after the injections in all seven subjects.

Local injection into the TrP of 5–10 mg of phentolamine in 1 cc of normal saline produced a rapid reduction of trigger point activity. This reduction was maximal at 20–30 minutes. The reduction affected both amplitude and frequency of EMG spontaneous activity in active trigger points. The EMG activity in the adjacent non-tender site did not change. In three of the four studies, the EMG activity returned within 40 minutes. FIG. 5 shows the progressive reduction and return of trigger point activity in a normal subject. The top tracing is prior to phentolamine injection and each subsequent tracing is at 5-minute intervals after injection. Only the trigger point EMG tracings are presented since non-tender site tracings remained silent. FIG. 6 shows the trigger point EMG changes in a normal subject. The left frame shows the trigger point and non-tender EMG activity before phentolamine. At 20 minutes after sympathetic blockade (middle frame) the trigger point EMG activity is virtually indistinguishable from the adjacent non-tender site activity. At 40 minutes (right frame) the trigger point activity has partially returned. FIG. 7 presents the phentolamine responses from a chronic tension headache patient. Note that the gain in the patient tracings is half that of the normal subject tracings. At 30 minutes (middle frame) the activity is reduced but still present, at 50 minutes (right frame) the trigger point activity has returned. Injection of 9.5ml of sterile water into the same trigger point several weeks later produced no reduction in spontaneous activity. FIG. 8 shows the mean and s.d. of mean EMG amplitude before and 5 minutes after the injections in all seven subjects.

Figure 9:
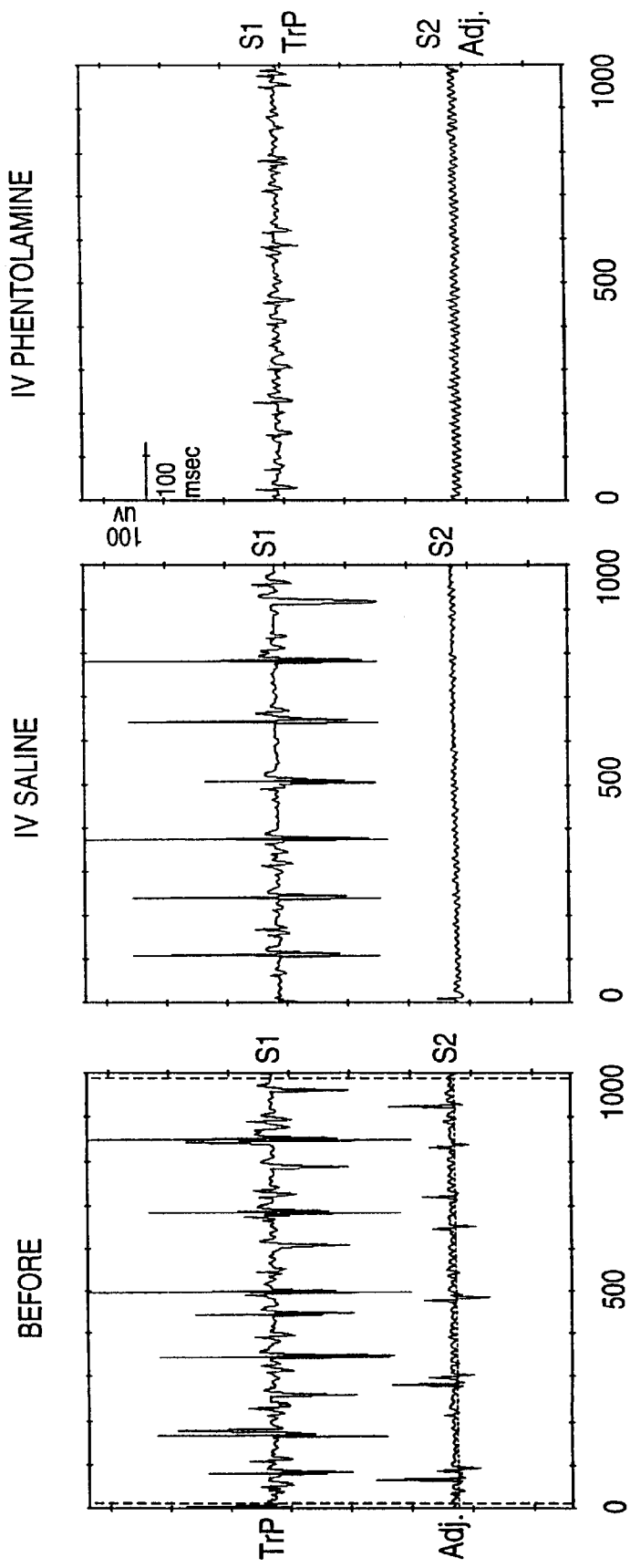
FIG. 9 is an electromyograph recording showing the response in one of the subjects before (left frame) during saline infusion (middle frame) and during the phentolamine infusion (right frame).

Another group of two patients received the phentolamine intravenously. One was a 36 year old man with an active trigger point in the right brachioradialis muscle, the other was a 31 year old woman with an active trigger point in her left trapezium. Phentolamine 10 mg in 100 cc normal saline was infused into the antecuboidal vein over 12 minutes using an indwelling intravenous line. In both studies, the trigger point EMG activity was eliminated during the infusion. FIG. 9 shows the response in one of the subjects before (left frame) during saline infusion (middle frame) and during the phentolamine infusion (right frame).

Another group of subjects received intramuscular injection of lidocaine or bupivacaine directly into a TrP. All injections were performed during EMG recording and the effects of the drugs upon EMG activity compared. Each of the drugs tested was prepared according to the manufacturer's directions. Phentolamine, lidocaine and bupivacaine all eliminated the TrP EMG activity within 2–20 minutes.

This study verified that spontaneous electrical activity of TrPs, which correlates with chronic pain, could be inhibited by a sympathetic antagonist.

Example 4

Method of Treating Chronic Muscle Pain by Delivering Phenoxybenzamine to a Trigger Point The purpose of this study was to determine whether delivery of a long-lasting adrenergic antagonist to a TrP would inhibit spontaneous electrical activity in the TrP and thereby reduce or eliminate the associated chronic pain. Sixteen subjects presenting with myofascial trigger point pain syndromes according to the criteria of Travell and Simons were included in the test group. The patients were treated with a single injection of phenoxybenzamine in an active trigger point. The mean age was 51, with a range between 33 to 72 years of age. Four of the patients were male and 12 were female. Half of the patients received their injection in the right side and half received the injection in their left side.

Trigger points were identified by manual palpation as described in Example 1. After an evaluation of active trigger points patients were asked to rate pain severity in (1) the myofascial region, including referral zone, chosen to be treated, (2) the overall body pain, including the trigger point area to be treated, and (3) in the injection site area. The pain severity evaluation was completed using daily visual analogue scales (VAS). They were asked to keep visual analogue pain diaries for one week prior, one week post injection as well as one week per month 1, 2 and 4 following the injection. Patients were also asked to keep track of their adverse events by reporting them at their next visits or by phone contact with the office.

A TECA monopolar EMG needle was inserted over the trigger point and advanced in 1 mm increments until the EMG spike activity was detected and the patient reported the characteristic trigger point pain and referral pattern. A second needle was placed adjacent to the trigger point needle in a non-tender area at a distance of 1 cm. Both needles were referenced to the same surface electrode. Trigger points were identified in the following muscles of the patients: trapezium, gluteus medius, suboccipital, multifidus, and quadratus lumborum.

Phenoxybenzamine (Dibenzyline injectable, SmithKline Beecham), 25 mg in 2cc of normal saline, was injected into the trigger point by inserting a 21 gauge, 2 inch hypodermic needle alongside of and to the same depth as the trigger point EMG needle. The subjects continued the daily VAS diaries and were re-evaluated at one and four weeks after injection.

VAS pain rating changes for the myofascial region are shown in Table 3. The values are percent improvement over time compared to their pain ratings prior to receiving the injection. Three patients failed to complete their pain diaries on monthly follow-up. Two patients were improved in the one week following treatment. Fifty percent of the patients were improved at one month post injection. This effect continued across the four month follow-up.

TABLE 3

TRIGGER POINT INJECTION WITH PHENOXYBENZAMINE
SINGLE INJECTION
Values are based on changes in daily visual analog ratings across time
16 Patients were injected with 25 mg of phenoxybenzamine in normal saline

|  | 1 Week | 1 Month | 2 Months | 4 Months |
| --- | --- | --- | --- | --- |
| Number of Patients Evaluated | 15 | 14 | 12 | 13 |
| 75 to 100% improved | 2 | 7 | 3 | 5 |
| 50 to 74% improved | 1 | 1 | 4 | 1 |
| 25 to 49% improved | 3 | 0 | 1 | 1 |
| unchanged | 5 | 3 | 4 | 3 |

TABLE 3-continued

TRIGGER POINT INJECTION WITH PHENOXYBENZAMINE
SINGLE INJECTION
Values are based on changes in daily visual analog ratings across time
16 Patients were injected with 25 mg of phenoxybenzamine in normal saline

|  | 1 Week | 1 Month | 2 Months | 4 Months |
| --- | --- | --- | --- | --- |
| worsened | 4 | 3 | 0 | 3 |
| Drop outs | 1 | 2 | 4 | 3 |

In another study using the same protocol as above, eight patients with myofascial pain were treated using a single injection of phenoxybenzamine, 12.5 mg in 0.5cc normal saline, in an active trigger point. The mean age of the patents was 44.8, with a range between 29 and 71 years of age. Two males and six females were treated. Two patients were treated on the left side of their bodies with six treated on their right. VAS pain rating changes for the myofascial region are represented in Table 4.

TABLE 4

TRIGGER POINT INJECTION WITH PHENOXYBENZAMINE
SINGLE INJECTION
Values are based on changes in daily visual analog ratings across time
8 Patients were injected with 12.5 mg of phenoxybenzamine in normal saline

|  | 1 Week | 1 Month | 2 Months | 4 Months |
| --- | --- | --- | --- | --- |
| Number of Patients Evaluated | 7 | 6 | 6 | 3 |
| 75 to 100% improved | 3 | 2 | 4 | 2 |
| 50 to 74% improved | 0 | 1 | 0 | 1 |
| 25 to 49% improved | 3 | 0 | 1 | 0 |
| unchanged | 0 | 0 | 0 | 0 |
| worsened | 1 | 1 | 1 | 0 |
| Drop outs | 1 | 2 | 2 | 5 |

These values are calculated by subtracting the average for the one week post from the average of the one week before injection divided by the mean of one week before injection resulting in a percent improvement. Each patient's score is then categorized into 75 to 100% improved, 50 to 74% improved, 25 to 49% improved, unchanged, or worsened. Three out of the seven evaluated at one week post reported 75 to 100% improvement. Improvement scores were consistent over the four month follow-up.

In another study using the same protocol as above, eighty-four myofascial pain patients were treated with multiple injections of phenoxybenzamine, 10 mg in 0.5cc normal saline. The mean age of the patients was 52.2 years, with a range between 24 to 80 years of age. Fifty-nine patients were female and 25 were male. Eighty-four percent of the patients chose to have their head and neck pain treated, 9% had their head, neck, and arm pain treated, and 7% had their low back pain treated. Forty-four percent of the patients had their left side treated and 56% had their right side treated. In addition, patients were asked to rate their pain according to the following categories: 1) much improved, 2) somewhat improved, 3) unchanged, 4) somewhat worse, and 5) much worse. The patients improvement based on changed in their VAS diaries are reported in Table 5.

TABLE 5

TRIGGER POINT INJECTION WITH PHENOXYBENZAMINE
MULTIPLE INJECTION
Values are based on changes in daily visual analog rafings across time
84 Patients were injected with phenoxybenzamine

|  | 1 Month | 2 Months | 3 Months | 4 Months |
|---|---|---|---|---|
| Number of Patients Evaluated | 66 | 60 | 49 | 43 |
| 75 to 100% improved | 15 | 18 | 11 | 6 |
| 50 to 74% improved | 8 | 10 | 11 | 9 |
| 25 to 49% improved | 12 | 13 | 9 | 10 |
| unchanged | 20 | 14 | 10 | 12 |
| worsened | 11 | 5 | 8 | 6 |

This study presently is in its follow-up phase, so that not all patients have completed the protocol. Twenty-three percent of those evaluated at one month post injection reported 75–100% improvement, 30% at two months, 22% at three months, and 14% at four months. When the patient's categorical ratings are evaluated, 29% report being much improved at one month, 32% at two months, 33% at three months, and 28% at four months.

The following adverse effects were reported: pain at injection site, swelling at injection site, pain in shoulder, shortness of breath, tachycardia, palpitations, knee paresthesias, muscle spasms in foot, medicine taste in mouth, shoulder pain, difficulty swallowing, dryness of nasal passages, light-headedness and cholecystectomy. In keeping with the FDA protocol, all events transpiring after injection were treated as adverse events regardless of judgment of relatedness. All reported events were self-limited and none required treatment. There were no serious, life-threatening adverse events.

Thus, the study demonstrated successful long-term reduction or elimination of pain by delivering a long-term adrenergic antagonist to a TrP. This study suggests that such delivery provides an attractive method for treating chronic muscle pain.

Example 5

Method of Determining Efficacy of Treating Pain by Delivering Phenoxybenzamine to a Myofascial Trigger Point A study similar to that described in Example 4 is carried out to evaluate the efficacy of treatment of myofascial trigger points associated with fibromyalgia with the sympathetic blocker phenoxybenzamine, the local anesthetic lidocaine and normal saline (control). It is hypothesized that local sympathetic blockade of myofascial trigger points will produce long-lasting reduction of pain and tenderness to palpation as compared to treatment with local anesthetic.

Patients presenting to the Neurologic Centre for Headache and Pain with a clinical diagnosis of fibromyalgia are invited to participate.

| Inclusionary criteria: | Exclusionary criteria: |
|---|---|
| 1. diagnosis of fibromyalgia according to the American College of Rheumatology criteria | 1. hypotension |
| 2. males and females between 20 and 60 | 2. concomitant use of sympathetic or mimetic medications such as propranolol |
| 3. no other clinically signfflcant medical or psychiatric problems | |
| 4. informed consent | |

All patients in the group are evaluated by a board-certified neurologist. The patients are then randomly assigned to either the phenoxybenzamine test group, the lidocaine test group or the saline control group. Neither the patients nor the physician assigned to evaluate the pre-and post-treatment symptoms are aware of the treatment group to which the patient is assigned.

Myofascial trigger points are identified by manual palpation according to the criteria of Simons and Travell:
 palpable firmness within the muscle
 tenderness to palpation
 typical referral pattern of pain
 local twitch response (not required for inclusion)
 Identified TrPs are examined by needle EMG. If spontaneous spike activity greater than 50 $\mu V$ is identified (as described in Example 1) then one of phenoxybenzamine (10 mg), lidocaine (2%) or saline is injected directly into the TrP in a volume of 1 cc.

Following injection blood pressure and heart rate are monitored for 30 minutes. The patient is then asked to keep a daily pain log employing the VAS ratings and to return at weekly intervals for one month, then at monthly intervals for 4 months. Self-report of pain, tenderness and firmness of the TrPs or TePs to palpation, medication use, and functional disability (time at bed rest, time lost from work) are assessed at weekly intervals for one month, then at monthly intervals for 4 months. Post-injection scores for each interval are compared to pre-injection scores and the relative efficacy of the treatments determined.

Example 6

Method of Treating of Chronic Myofascial Pain With Other Sympathetic Antagonists A study similar to that described in Example 5 is carried out to evaluate the efficacy and safety of treatment of myofascial trigger points associated with fibromyalgia with sympathetic blockers such as guanethidine. The relative efficacy and safety of treatment with these other antagonists are compared to that of phenoxybenzamine.

Patients presenting to the Neurologic Centre for Headache and Pain with a clinical diagnosis of fibromyalgia and who meet the inclusionary criteria described in Example 5 are invited to participate. All patients in the group are evaluated by a board-certified neurologist. The patients are then randomly assigned to the guanethidine test group, the phenoxybenzamine standard group or the saline control group. Neither the patients nor the physician assigned to perform the pre- and post-treatment assessment are aware of the treatment received by the patient.

Myofascial trigger points are identified by manual palpation according to the criteria of Simons and Travell as described in Example 5.

If spontaneous spike activity is identified as described in Example 1, then either phenoxybenzamine (10 mg) guanethidine (10 mg) or normal saline (1 cc) is injected directly into the TrP.

Following injection, blood pressure and heart rate are monitored for 30 minutes. The patient is then asked to keep a daily pain log employing the VAS ratings and to return at weekly intervals for one month, then at monthly intervals for 4 months. Self-report of pain, and tenderness and firmness to palpation, and medication use, and functional disability (time at bed rest, time lost from work) are assessed at weekly intervals for one month, then at monthly intervals for 4 months. Post-injection scores for each interval are compared to pre-injection scores.

Example 7

Method of Treating of Related Muscle Pain Conditions with a Sympathetic Antagonist The purpose of this study is to determine whether delivery of a sympathetic antagonist to various localized regions which have spontaneous electrical activity inhibits that activity and reduces pain. A study similar to that described in Example 5 is carried out to determine the efficacy of local sympathetic antagonist injection in treating other muscle pain conditions such as fibromyalgia with and without trigger points, chronic strain injuries and low back syndrome.

Patients presenting with a clinical diagnosis of fibromyalgia with and without trigger points, chronic strain injuries or low back syndrome are invited to participate. Inclusionary and exclusionary criteria for participation in the patient groups are described in Example 5. All patients in the group are evaluated by a board-certified neurologist. The patients are then randomly assigned to either the phenoxybenzamine test group or the saline control group. Neither the patients nor the physician assigned to evaluate the pre- and post-treatment symptoms are aware of the treatment the patient has received.

When appropriate, myofascial TrPs are identified by manual palpation according to the criteria of Simons and Travell as described in Example 5.

If spontaneous spike activity (as described in Example 1) is identified then either phenoxybenzamine (5 mg) or saline is injected directly into the TrP in a volume of 1 cc. In patients presenting with fibromyalgia without trigger points, chronic muscle strain or low back syndrome, either phenoxybenzamine (10 mg) or saline (1 cc) is injected into the areas of painful muscles.

Following injection, blood pressure and heart rate are monitored for 30 minutes. The patient is then asked to keep a daily pain log employing the VAS ratings and to return at weekly intervals for one month, then at monthly intervals for 4 months. Self-report of pain, tenderness and firmness of the TrPs or TePs to palpation, medication use, and functional disability (time at bed rest, time lost from work) are assessed at weekly intervals for one month, then at monthly intervals for 4 months. Post-injection scores for each interval are compared to pre-injection scores and the relative efficacy of the treatments determined.

This study demonstrates that the above-described method is broadly applicable to a variety of pain conditions that are associated with neuromuscular abnormalities.

Each year chronic muscle pain affects 24 million Americans and results in 4.1 million hospitalizations, 3.75 million operations (11.5% of all operations), and 30 million office visits. The lifetime prevalence of low back pain lasting 1 or more days of the American population is 56%, 70% of whom consulted physicians. Approximately 21 million persons suffer low back pain per year, resulting in a total annual cost of between $20–56 billion. Of those patients with low back pain lasting more that 2 weeks, 31% are hospitalized, and 11.6% undergo surgery. Only 1% of low back pain sufferers have surgical lumbar disk disease; surgery to remedy this, condition is associated with a 15–30% failure rate, where return to the same occupation is used as a measure of the outcome. The principal reason for failure is incorrect diagnosis. Ironically, psychologic evaluation seems more predictive of a successful outcome following surgery than the current diagnostic studies or surgical findings.

The prevalence of other neuromuscular disorders besides back pain is 53%. Of that percentage, headaches account for 73% and temporomandibular disorders for 12.3%. Both of these conditions are primarily muscular in nature. The total annual cost of headaches alone is $16 billion, while the total annual cost for all other neuromuscular disorders is $11 billion.

As is apparent from these statistics, chronic muscle pain is one of the most common medical conditions and accounts for enormous costs both in medical bills and disability. Applicant has described a mechanism of pathogenesis for chronic pain; in short, the sympathetic activity provides a mechanism by which local injury and noninception causes local tension and by which emotional factors cause widespread tension and pain. The subject invention provides an objective method of diagnosis and evaluation of chronic pain and improved treatment regimen which take advantage of this mechanism.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for reducing chronic pain comprising:
   locating at least one myofascial trigger point in a muscle; and
   contacting the myofascial trigger point with a sufficient amount of phenoxybenzamine, to inhibit spontaneous EMG spike activity in said myofascial trigger point, whereby said chronic pain is reduced.

2. A method of claim 1, wherein said contacting is with 1–50 mg of phenoxybenzamine.

3. A method of claim 1, wherein said contacting is by direct injection into said trigger point.

4. A method of claim 1, wherein said contacting is by local injection.

5. A method of claim 1, wherein said contacting is by local injection into area of painful muscle.

6. A method of claim 1, wherein said contacting is by intramuscular injection.

7. A method of claim 1, further comprising detecting spontaneous EMG activity associated with said trigger point prior to said contacting the myofascial trigger point.

8. A method of claim 1, wherein said locating is identifying a palpable firm area of muscle having a localized spot tender to manual pressure.

9. A method of claim 1, wherein said locating is identifying a palpable firm area of muscle having a localized spot tender to manual pressure and applying pressure to said area in an amount effective to elicit pain, tingling, or numbness.

10. A method of claim 1, wherein said locating is identifying a palpable firm area of muscle having a localized spot tender to manual pressure; applying pressure to said area in an amount sufficient to elicit pain, tingling, or numbness; and distorting said area traversely, whereby a twitch is elicited.

11. A method for reducing chronic pain comprising:
locating at least one myofascial trigger point in a muscle; and
contacting the myofascial trigger point with a sufficient amount of phentolamine, guanethidine, tolazoline, prazosin, terzosin, doxazosin, trimazosin, indoramin, dibenamine, guanadrel, reserpine, or meyrosine, to inhibit spontaneous EMG spike activity in said myofascial trigger point, whereby said chronic pain is reduced.

12. A method of claim 11, wherein said contacting is with 2–100 mg of phentolamine.

13. A method of claim 11, wherein said contacting is with 10–100 mg of guanethidine.

14. A method of claim 11, wherein said contacting is by direct injection into said trigger point.

15. A method of claim 11, wherein said contacting is by local injection.

16. A method of claim 11, wherein said contacting is by local injection into an area of painful muscle.

17. A method of claim 11, wherein said contacting is by intramuscular injection.

18. A method of claim 11, further comprising detecting spontaneous EMG activity associated with said trigger point prior to said contacting the myofascial trigger point.

19. A method for reducing chronic pain comprising:
locating at least one myofascial trigger point in a muscle comprising at least one muscle spindle; and
contacting the myofascial trigger point with a sufficient amount of an agent which inhibits the spontaneous activity of said muscle spindle, whereby said chronic pain is reduced.

20. A method of claim 19, wherein the agent is a sympathetic blocking agent or an agent which depletes a neurotransmitter.

21. A method of claim 19, wherein the agent binds to an alpha adrenergic receptor.

22. A method of claim 19, wherein the agent is an alpha adrenergic antagonist.

23. A method of claim 22, wherein the antagonist is an irreversible antagonist.

24. A method of claim 19, wherein said contacting is by local injection.

25. A method of claim 19, wherein said contacting is by intramuscular injection.

26. A method of claim 19, wherein said contacting of said trigger point occurs in a head, neck, extremity, or back muscle.

27. A method of claim 19, wherein said contacting of said trigger point occurs in a trapezius muscle.

28. A method of claim 19, wherein the trigger point has a mean EMG amplitude of at least 40 $\mu V$ prior to the contacting.

29. A method of claim 19, wherein said locating is by detecting spontaneous EMG activity of the trigger point.

30. A method of claim 19, further comprising administering a local anesthetic in combination with the agent.

31. A method of claim 19, wherein said agent is not a local anesthetic.

32. A method of claim 19, wherein said contacting is by direct injection into said trigger point.

33. A method of claim 19, wherein said contacting is by local injection into an area of painful muscle.

34. A method of claim 19, further comprising detecting spontaneous EMG activity associated with said trigger point prior to said contacting the myofascial trigger point.

35. A method for reducing chronic pain comprising:
locating at least one neuromuscular abnormality in a muscle comprising at least one muscle spindle; and
contacting said neuromuscular abnormality with a sufficient amount of an agent which blocks the spontaneous activity of said muscle spindle, whereby said chronic pain is reduced.

36. A method of claim 35, wherein the neuromuscular abnormality comprises a trigger point or a tender point.

37. A method of claim 35, wherein the neuromuscular abnormality is a dysfunction of skeletal muscle.

38. A method of claim 35, wherein the neuromuscular abnormality is fibromyalgia or myofascial pain syndrome.

39. A method of claim 35, wherein the neuromuscular abnormality comprises a chronic headache.

40. A method of claim 35, wherein said agent is not a local anesthetic.

41. A method of claim 35, wherein the agent is a sympathetic blocking agent or an agent which depletes a neurotransmitter.

42. A method of claim 35, wherein the agent binds to an alpha adrenergic receptor.

43. A method of claim 35, wherein the agent is an alpha adrenergic antagonist.

44. A method of claim 35, wherein the antagonist is an irreversible antagonist.

45. A method of claim 35, wherein said contacting is by local injection.

46. A method of claim 35, wherein said contacting is by intramuscular injection.

47. A method of claim 35, wherein said contacting is by injection into an area of painful muscle.

48. A method of claim 35, further comprising detecting spontaneous EMG activity associated with said trigger point prior to said contacting the myofascial trigger point.

49. A method for identifying patients with chronic pain susceptible to treatment with phenoxybenzamine, said method comprising:
locating at least one myofascial trigger point, having spontaneous EMG activity, within a muscle causing said chronic pain; and
contacting said myofascial trigger point with phenoxybenzamine, whereby said patients with chronic pain susceptible to treatment are identified by a reduction in said spontaneous EMG spike activity.

50. A method for identifying patients with chronic pain susceptible to treatment with a sufficient amount of phentolamine, guanethidine, tolazoline, prazosin, terzosin, doxazosin, trimazosin, indoramin, dibenamine, guanadrel, reserpine, or meyrosine, to inhibit spontaneous EMG spike activity in said myofascial trigger point, whereby said chronic pain is reduced, said method comprising:
locating at least one myofascial trigger point, having spontaneous EMG activity, within a muscle causing said chronic pain; and
contacting said myofascial trigger point with a sufficient amount of phentolamine, guanethidine, tolazoline, prazosin, terzosin, doxazosin, trimazosin, indoramin, dibenamine, guanadrel, reserpine, meyrosine, to inhibit spontaneous EMG spike activity in said myofascial trigger point, whereby said patients with chronic pain susceptible to treatment are identified by a reduction in said spontaneous EMG spike activity.

51. A method for identifying patients with chronic pain susceptible to treatment with an agent which blocks the spontaneous activity of a muscle spindle, said method comprising:

locating at least one myofascial trigger point comprising at least one muscle spindle, having spontaneous EMG activity, within a muscle causing said chronic pain; and contacting said myofascial trigger point with an agent which blocks the spontaneous activity of said muscle spindle, whereby said patients with chronic pain susceptible to treatment are identified by a reduction in said spontaneous EMG spike activity.

52. A method for identifying patients with chronic pain susceptible to treatment with an agent which blocks the spontaneous activity of a muscle spindle, said method comprising:

locating at least one neuromuscular abnormalities comprising at least one muscle spindle, having spontaneous EMG activity, within a muscle causing said chronic pain; and contacting said neuromuscular abnormality with a sufficient amount of an agent which blocks the spontaneous activity of said muscle spindle, whereby said patients with chronic pain susceptible to treatment are identified by a reduction in said spontaneous EMG spike activity.

53. A method for treating chronic muscle pain comprising: locating at least myofascial trigger point in a muscle; and contacting the myofascial trigger point with an amount of phenoxybenzamine effective to treat said chronic pain.

54. A method for treating chronic muscle pain comprising: locating a neuromuscular abnormality; and contacting the neuromuscular abnormality with an amount of phenoxybenzamine effective to treat said chronic pain.

55. A method for reducing chronic muscle pain comprising: injecting an amount of phenoxybenzamine into a myofascial trigger point of a muscle effective to reduce said chronic pain.

56. A method of claim 55, wherein said injection is directly into said trigger point.

57. A method of claim 55, wherein said injection is a local injection.

58. A method of claim 55, wherein said injection is into a painful area of said muscle.

59. A method of claim 55, wherein said injection is an intramuscular injection.

60. A method of reducing chronic muscle pain comprising: injecting an amount of phenoxybenzamine into a neuromuscular abnormality effective to reduce said chronic pain.

61. A method of treating chronic muscle pain comprising: administering directly or locally into a myofascial trigger point of a muscle or into a neuromuscular abnormality an amount of phenoxybenzamine effective to treat said chronic pain.

* * * * *